US010241100B2

(12) United States Patent
Xu et al.

(10) Patent No.: US 10,241,100 B2
(45) Date of Patent: Mar. 26, 2019

(54) METHOD FOR DETERMINING RESIDUAL SURFACTANT CONCENTRATIONS IN PRODUCED WATER

(71) Applicant: Halliburton Energy Services, Inc., Houston, TX (US)

(72) Inventors: Liang Xu, Houston, TX (US); Qiang Fu, Houston, TX (US); Jayant Rane, Kingwood, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 0 days.

(21) Appl. No.: 14/228,152

(22) Filed: Mar. 27, 2014

(65) Prior Publication Data

US 2015/0275627 A1 Oct. 1, 2015

(51) Int. Cl.
*E21B 49/08* (2006.01)
*G01N 33/18* (2006.01)
*G01N 13/02* (2006.01)
*E21B 43/00* (2006.01)
*E21B 44/00* (2006.01)
*G01N 30/96* (2006.01)
*G01N 33/28* (2006.01)

(52) U.S. Cl.
CPC ......... *G01N 33/1826* (2013.01); *G01N 13/02* (2013.01); *E21B 43/00* (2013.01); *E21B 44/00* (2013.01); *E21B 49/08* (2013.01); *G01N 30/96* (2013.01); *G01N 33/2823* (2013.01)

(58) Field of Classification Search
CPC ......... E21B 49/08; E21B 43/00; E21B 44/00; G01N 1/00; G01N 13/00; G01N 15/00

USPC .................. 166/369, 250.01, 264
See application file for complete search history.

(56) References Cited

U.S. PATENT DOCUMENTS 3,722,595 A * 3/1973 Kiel .................... C09K 8/64
166/308.4
4,253,974 A 3/1981 Valcho et al.
(Continued)

FOREIGN PATENT DOCUMENTS

GB 2410550 A * 8/2005
WO 2000/00815 A1 1/2000

OTHER PUBLICATIONS

Examination Report; Australian Application No. 2014262209; dated Apr. 19, 2016.
(Continued)

*Primary Examiner* — Silvana C Runyan
(74) *Attorney, Agent, or Firm* — Polsinelli PC

(57) ABSTRACT

A method for determining a first concentration of a first component in an aqueous solution, the surface tension of which is altered by the presence of the first component. The method can include identifying a second concentration of at least one second component in the aqueous solution. The at least one second component can also alter the surface tension of the aqueous solution. The method can further include comparing a plurality of dynamic surface tension measurements of each of a plurality of aqueous test solutions with at least one dynamic surface tension measurement of the aqueous solution to determine the first concentration. The plurality of aqueous test solutions can include the first component at a plurality of concentrations and the at least one second component at the second concentration.

11 Claims, 15 Drawing Sheets

(56) References Cited

U.S. PATENT DOCUMENTS

| | | | |
|---|---|---|---|
| 5,033,547 A | 7/1991 | Schievelbein | |
| 7,481,097 B2* | 1/2009 | Schumann et al. | 73/64.51 |
| 2007/0295368 A1* | 12/2007 | Harrison et al. | 134/42 |
| 2010/0059226 A1* | 3/2010 | Termine et al. | 166/308.1 |
| 2013/0067999 A1* | 3/2013 | Xu et al. | 73/64.51 |

OTHER PUBLICATIONS

ISO 7875-1, Second Edition, Water quality. Determination of Surfactants. Part 1: Determination of Anionic Surfactants by Measurement of the Methylene Blue Index (MBAS). ISO/TC 147, Dec. 15, 1996; downloaded Nov. 18, 2013.

Chitikela, S., Dentel, S.K., Allen, H.E., 1995. Modified method for the analysis of anionic surfactants as methylene blue active substances. Analyst vol. 120, pp. 2001-2004, Jul. 1995.

Koga, M., Yamamichi, Y., Nomoto, Y., Irie, M., 1999. Rapid determination of anionic surfactants by improved spectrophotometric method using methylene blue. Anal. Sci. vol. 15, 563-568, Jun. 1999.

SensaDyne Instrument Division, Surface Tension Tutorial; Dynamic Surface Tension Measurement Tutorial, www.sensadyne.com/surface-tension-tutorial; retrieved Nov. 19, 2013.

ISO, Determination of anionic surfactants by measurement of the methylene blue index (MBAS), Technical Corrigendum 1 to ISO 7875-1:1996 was prepared by Technical Committee ISO/TC 147, Water Quality, Subcommittee SC 2, Physical, chemical and biochemical methods , Published Jul. 1, 2003.

NC, Christov, Maximum bubble pressure method: Universal surface age and transport mechanisms in surfactant solutions, www.ncbi.nlm.nih.gov/pubmed/16922530; Aug. 29, 2006; 22(18):7528-42.

Examination Report; Australian Application No. 2014262209; dated Nov. 12, 2015.

* cited by examiner

METHOD FOR DETERMINING RESIDUAL SURFACTANT CONCENTRATIONS IN PRODUCED WATER

FIELD

The disclosure relates generally to a method for determining a first concentration of a first component in an aqueous solution and more specifically to a method for determining residual surfactant concentrations in produced water from an oil or gas well.

BACKGROUND

Surfactant is a chemical component in a hydraulic fracturing ("fracking") fluid which is usually used to enhance initial production and to possibly improve long term production of the reservoir. Different roles that surfactant play to increase the production are decreasing capillary pressure of the fracturing fluid inside formation rocks for effective flow back, possibly emulsifying more oil globules and droplets in the reservoir and possibly changing the wettability from oil-wet to water-wet, just to name a few. There has been a new trend of using weakly emulsifying surfactant (WE) in the field over non-emulsifying surfactant (NE) as WE surfactants seems to be effective in terms of enhanced oil recovery from various liquid rich shale plays across North America.

Surfactant has proven to be critical to enhance initial production and sustain long term production in low permeability oil and gas reservoirs. During hydraulic fracturing operations, surfactants are pumped together with other chemicals to target formation zones. Once surfactants reach downhole, they can interact specifically with oil molecules, strip them off the rock and mobilize them through the reservoir. For those mechanisms to deploy, it is believed that surfactants should remain in the reservoir. To ensure optimum application of surfactants, operating and service companies have been searching for tools for tracking surfactant residuals in flow back and produced waters, which is thought to be possibly correlated with well productivity. One of the methods for determining how much surfactant is left in the reservoir is to monitor surfactant residuals in produced waters. Because of the presence of various total dissolved solids (TDS) levels and other fracturing additives such as friction reducers, scale inhibitors or biocides, it is not an easy task to track surfactant residuals. Conventional methods such as methylene blue (MB) based absorbance measurements take into account the bonding between anionic surfactants and cationic MB, but MB would bond with anything that is anionic in produced waters, resulting in erroneous analysis. Therefore, following the conventional dye based approach, such as methylene blue that typically combines with anionic surfactants, requires that the concentration of the combined complex be determined by using spectroscopic methods. This approach, however, can lead to erroneous results because of the presence of anionic friction reducers, scale inhibitor and/or gelled fluids.

BRIEF DESCRIPTION OF THE DRAWINGS

These and other features, aspects, and advantages of the present disclosure will become better understood with reference to the following description and appended claims, and accompanying drawings where:

FIG. 4($b$) is a chart showing a calibration curve of the slope of the short time kinetics region plotted against concentration of surfactants;

FIG. 5($b$) is a chart showing a calibration curve of absorbance at 210-240 nm wavelength plotted against surfactant concentration;

FIG. 6($b$) is a chart showing Prediction of about 600 ppm (572 ppm) surfactant concentration from a UV-Vis calibration curve;

FIG. 8($b$) is a chart showing surface tension against square root of time for those concentrations;

Figure 1:
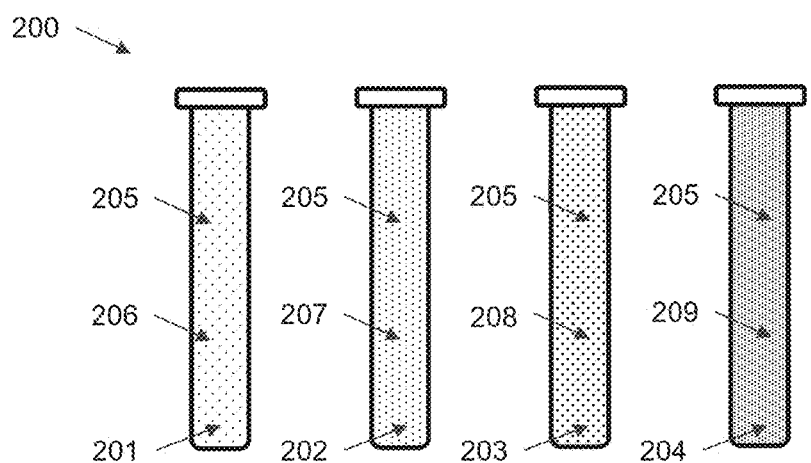
FIG. 1 is a schematic illustration of a plurality of aqueous test solutions.

It should be understood that the various embodiments are not limited to the arrangements and instrumentality shown in the drawings.

DETAILED DESCRIPTION

The present disclosure may be understood more readily by reference to the following detailed description of preferred embodiments of the disclosure as well as to the examples included therein. All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

One embodiment relates to a method for determining a first concentration of a first component in an aqueous solution. Various embodiments take advantage of dynamic diffusion profiles between liquid phases at different surfactant concentrations, which are unique to each individual surfactant. To determine the first concentration of the first component in the aqueous solution, the method can include a step of identifying a second concentration of at least one second component in the aqueous solution. The second concentration can be identified by any conventional means, including but not limited to spectroscopy. Additionally or alternatively, to identify the second component such as a scale inhibitor, a colormetric method can be used. In particular, the tagging agent on the scale inhibitor can be reacted with the test solution and its concentration can be measured by contacting the reacted test solutions with colormetric paper.

Both the first component and the second component can alter the surface tension of the aqueous solution.

The first component can be a surfactant. For example, the first component can be a nonionic surfactant, an ionic surfactant, an amphoteric surfactant, or any combination of surfactants.

As used herein, a "nonionic surfactant" refers to a surfactant in which the molecules forming the surfactant are uncharged. Suitable nonionic surfactant can include, but are not limited to condensation products of ethylene oxide with phenols, naphthols, and alkyl phenols, for example octyphenoxy-nonaoxyethyleneethanol. Examples for nonionic surfactants include, but are not limited to ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, ii polyoxyethylene octylphenylether, PEG-1000 cetyl ether, polyoxyethylene tridecyl ether, polypropylene glycol butyl ether, a nonionic triblock copolymer composed of a central hydrophobic chain of polyoxypropylene (poly(propylene oxide)) flanked by two hydrophilic chains of polyoxyethylene (poly (ethylene oxide)), such as stearoyl monoisopropanolamide, and polyoxyethylene hydrogenated tallow amide. Other examples of nonionic surfactants include but are not limited to fatty acid glycerine esters, sorbitan fatty acid esters, sucrose fatty acid esters, polyglycerine fatty acid esters, higher alcohol ethylene oxide adducts, single long chain polyoxyethylene alkyl ethers, polyoxyethylene alkyl allyl ethers, polyoxyethylene lanolin alcohol, polyoxyethylene fatty acid esters, polyoxyethylene glycerine fatty acid esters, polyoxyethylene propylene glycol fatty acid esters, polyoxyethylene sorbitol fatty acid esters, polyoxyethylene castor oil or hardened castor oil derivatives, polyoxyethylene lanolin derivatives, polyoxyethylene fatty acid amides, polyoxyethylene alkyl amines, an alkylpyrrolidone, glucamides, alkylpolyglucosides, mono- and dialkanol amides, a polyoxyethylene alcohol mono- or diamides and alkylamine oxides.

As used herein, an "ionic surfactant" refers to a surfactant in which the molecules forming the surfactant are charged. Suitable ionic surfactants can include but are not limited to sulfonates, sulfates, ammonium, phosphonium, and sulphonium alkylated quaternary or ternary compounds, singly or attached to polymeric compounds. Suitable anionic surfactants include, but are not limited to those containing carboxylate, sulfonate, and sulfate ions. Examples of anionic surfactants, include but are not limited to sodium, potassium, ammonium of long chain alkyl sulfonates and alkyl aryl sulfonates such as sodium dodecylbenZene sulfonate; dialkyl sodium sulfosuccinates, such as sodium dodecylbenZene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to quaternary ammonium compounds such as benZalkonium chloride, benZethonium chloride, cetrimonium bromide, stearyl dimethylbenZyl ammonium chloride, polyoxyethylene (15), and coconut amine. Examples of the anionic surfactants include but are not limited to fatty acid soaps, ether carboxylic acids and salts thereof, alkane sulfonate salts, α-olefin sulfonate salts, sulfonate salts of higher fatty acid esters, higher alcohol sulfate ester salts, fatty alcohol ether sulfates salts, higher alcohol phosphate ester salts, fatty alcohol ether phosphate ester salts, condensates of higher fatty acids and amino acids, and collagen hydrolysate derivatives. Examples of the cationic surfactants include but are not limited to alkyltrimethylammonium salts, dialkyldimethylammonium salts, alkyldimethylbenzylammonium salts, alkylpyridinium salts, alkylisoquinolinium salts, benzethonium chloride, and acylamino acid type cationic surfactants.

As used herein, an "amphoteric surfactant" refers to a surfactant compound uniquely structured to function as cationic surfactants at acid pH and anionic surfactants at alkaline pH. Suitable amphoteric surfactants can include, but are not limited to amino acid, betaine, sultaine, phosphobetaines, imidazoline type amphoteric surfactants, soybean phospholipid, and yolk lecithin. Examples for amphoteric surfactants include, but are not limited to, sodium N-dodecyl-beta-alanine, sodium N-lauryl-beta-iminodipropionate, myristoamphoacetate, lauryl betaine, and laurylsulfobetaine.

Fracturing is the process of creating fractures in oil and gas formations to stimulate or increase production in oil and gas wells. The fracturing operation involves the injection of fracturing fluid into the wellbore at sufficient pressures, flow rates and volumes to fracture the surrounding formation. The fracturing fluid may comprise a base fluid, such as water or gels, and a variety of additives including polymers, friction reducers, cross-linkers, anti-scaling agents, proppants and biocides. The first component can also be an oil field chemical including, but not limited to production chemicals, fracturing fluid, surfactants, biocides, scale inhibitors, wax solvents, asphaltenes inhibitors, pour point depressants, biocides, water clarifiers, shale and clay stabilizers, emulsion breakers, antifoams, scale inhibitors, $H_2S$ and $O_2$ scavengers, corrosion inhibitors, and combinations thereof. Other oilfield additives that may also be added to the fracturing fluid include emulsion breakers, antifoams, scale inhibitors, $H_2S$ and $O_2$ scavengers, biocides, surface tension reducers, shale and clay stabilizers, paraffin/asphaltene inhibitors and corrosion inhibitors. The first component can be any component that afters the surface tension of the aqueous solution.

A plurality of aqueous test solutions can be prepared or otherwise obtained. The plurality of aqueous test solutions can include the first component at a plurality of concentrations and the at least one second component at the second concentration. For example, as illustrated in FIG. 1, a plurality 200 of aqueous test solutions 201, 202, 203, 204 are shown. The first aqueous test solution 201 includes a first component at a concentration 206 and a second component at a second concentration 205. The second aqueous test solution 202 includes a first component at a concentration 207 and a second component at the second concentration 205. The third aqueous test solution 203 includes a first component at a concentration 208 and a second component at the second concentration 205. The fourth aqueous test solution 204 includes a first component at a concentration 209 and a second component at the second concentration 205. The second concentration 205 of the second component can be the same in each of the plurality 200 of aqueous test solutions 201, 202, 203, 204. The concentrations 206, 207, 208, 209 of the first component can vary among the plurality 200 of aqueous test solutions 201, 202, 203, 204 such that the plurality 200 of aqueous test solutions 201, 202, 203, 204 includes the first component at a plurality of concentrations.

According to certain preferred embodiments, each of the plurality of aqueous test solutions can include a plurality of second components. The plurality of second components can be selected such that, but for the varying concentrations of the first component, the aqueous test solution mirrors the composition of the produced water from an oil well. For example, the plurality of second components can be selected such that the composition of the aqueous test solution includes the same concentration of each of a plurality of minerals in the produced water. Compounds that do not alter the surface tension of the produced water can be, but do not need to be included among the plurality of second components. According to various preferred embodiments, the aqueous test solution includes all surface tension altering compounds that are in the produced water at the same concentration as those compounds are present in the produced water.

The concentration of the first component in each aqueous test solution can be within a range having a lower limit and/or an upper limit. The range can include or exclude the lower limit and/or the upper limit. The lower limit and/or upper limit can be selected from 0.1, 0.5, 1, 5, 10, 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, 4500, 4600, 4700, 4800, 4900, 5000, 5100, 5200, 5300, 5400, 5500, 5600, 5700, 5800, 5900, 6000, 6100, 6200, 6300, 6400, 6500, 6600, 6700, 6800, 6900, 7000, 7100, 7200, 7300, 7400, 7500, 7600, 7700, 7800, 7900, 8000, 8100, 8200, 8300, 8400, 8500, 8600, 8700, 8800, 8900, 9000, 9100, 9200, 9300, 9400, 9500, 9600, 9700, 9800, 9900, 10000, 10100, 10200, 10300, 10400, 10500, 10600, 10700, 10800, 10900, 11000, 11100, 11200, 11300, 11400, 11500, 11600, 11700, 11800, 11900, 12000, 12100, 12200, 12300, 12400, 12500, 12600, 12700, 12800, 12900, 13000, 13100, 13200, 13300, 13400, 13500, 13600, 13700, 13800, 13900, 14000, 14100, 14200, 14300, 14400, 14500, 14600, 14700, 14800, 14900, 15000, 15100, 15200, 15300, 15400, 15500, 15600, 15700, 15800, 15900, 16000, 16100, 16200, 16300, 16400, 16500, 16600, 16700, 16800, 16900, 17000, 17100, 17200, 17300, 17400, 17500, 17600, 17700, 17800, 17900, 18000, 18100, 18200, 18300, 18400, 18500, 18600, 18700, 18800, 18900, 19000, 19100, 19200, 19300, 19400, 19500, 19600, 19700, 19800, 19900, 20000, 20100, 20200, 20300, 20400, 20500, 20600, 20700, 20800, 20900, 21000, 21100, 21200, 21300, 21400, 21500, 21600, 21700, 21800, 21900, 22000, 22100, 22200, 22300, 22400, 22500, 22600, 22700, 22800, 22900, and 23000 ppm. For example, according to certain preferred embodiments, the concentration of the first component in each aqueous test solution can be from 0.1 to 20000 ppm.

The aqueous solution can be produced water from an oil well. The produced water can be collected from the well head of the oil well. Again, to determine the first concentration of the first component in the aqueous solution, the method can include a step of identifying a second concentration of at least one second component in the aqueous solution. The second component can be any component that alters the surface tension of the aqueous solution. The second component can be any of the compounds identified above as preferable first components. Similarly, the first component can be any of the compounds identified below as preferable second components. The first and second components are preferably different compounds.

In addition to being any of the compounds identified above as possible first components, the at least one second component can be, a friction reducer, a scale inhibitor, surfactants, biocides, scale inhibitors, wax solvents, asphaltenes inhibitors, pour point depressants, demulsifiers, biocides, water clarifiers, shale and clay stabilizers, emulsion breakers, antifoams, scale inhibitors, $H_2S$ and $O_2$ scavengers, corrosion inhibitors, and combinations thereof.

The friction reducer can include, but is not limited to reducing agents that comprise polymers, including generally high molecular weight linear polymers or polymers that have been slightly crosslinked or drag reducing surfactant formulations, or a combination thereof. As used herein with reference to polymers, "high molecular weight" is meant to encompass those polymers having a molecular weight of from about 5 to about 25 million or more. These polymers may be pumped at low enough concentrations such that they do not significantly increase the viscosity of the fluid. Suitable polymers may include guar or a guar derived polymer. Examples of suitable synthetic polymers and copolymers include polymethylmethacrylate, polyethyleneoxide, polyacrylamide, polymethacrylamide, partially hydrolyzed polyacrylamide, cationic polyacrylamide derived polymers such as those obtained by radical polymerization of dimethylamino ethyl methacrylate (DMAEMA), 2-(methacryloyloxy)-ethyltrimethylammonium chloride (MADQUAT), methacrylamidopropyl trimethyl ammonium chloride (MAPTAC), or diallyldimethylammonium chloride (DADMAC), or anionic polymer such as polyAMPS (poly 2-acrylamido-2-methylpropane sulfonic acid), and the like. Examples of other suitable friction reducers include polyacrylamide derivatives which may be supplied as concentrated emulsified conventional drag reducing formulations, containing around 30% of active vinyl polymer. Other polymers include high-molecular weight polysaccharides composed of mannose and galactose sugars, or guar derivatives such as hydropropyl guar (HPG), carboxymethyl guar (CMG), and carboxymethylhydroxypropyl guar (CMHPG). Cellulose derivatives such as hydroxyethylcellulose (HEC) or hydroxypropylcellulose (HPC) and carboxymethylhydroxyethylcellulose (CMHEC) may also be used. Any useful polymer may be used in either crosslinked form, or without crosslinking in linear form.

The scale inhibitor can include, but is not limited to one or more additives such as polyphosphates, poly(meth)acrylates, phosphonates, aminophosphonates, polymeric carboxylic acids such as poly[maleic acid], and combinations thereof.

The emulsion breakers can be polyvalent metal salts, mineral acids, adsorbents, polyamines and polyacrylates and their derivatives, alkyl substituted benzene sulfonic acids, alkyl phenolic resins and their derivatives, substituted polyalcohols, and the like.

The biocides include, but are not limited to hypochlorites, such as sodium hypochlorite (bleach), potassium hypochlorite and calcium hypochlorite; sodium bromide; hydantoins; peracetic acid; chlorine dioxide; ozone; hydrogen peroxide; and halogenated isocyanurates, preferably sodium hypochlorite.

Wax solvents include, but are not limited to methyl methacrylate, butyl methacrylate, lauryl methacrylate, ethyl acrylate, butyl acrylate, arylonitrile, methacrylonitrile, 2-ethylhexyl methacrylate, 3,3-dimethoxypropyl acrylate, 3-methacryloxypropyl acrylate, 2-acetoxyethyl methacrylate, p-tolyl methacrylate, 2,2,3,3,4,4,4-heptafluorobutyl acrylate, ethyl 2-cyanoacrylate, N,N-dimethylacrylamide, 4-fluorophenyl acrylate, 2-methacryloxyethyl acrylate, propyl vinyl ketone, ethyl 2-chloro acrylate, glycidyl methacrylate, 3-methoxypropyl methacrylate, phenyl acrylate, 2-(trimethylsiloxy)ethyl methacrylate, 2-(methylsiloxy) ethyl methacrylate, allyl acrylate, allyl methacrylate, ethyleneglycol diacrylate, diethyleneglycol diacrylate, glycerol diacrylate, glyceryl triacrylate, ethyleneglycol dimethacrylate and hexamethylene diol diacrylate. The halocarbon compound bound to one terminal end of the block copolymer chain in the polymeric dispersant according to the present disclosure may be pentafluorobenzyl bromide, 2,3, 5,6-tetrafluoro-4-(trifluoromethyl)benzyl bromide, 3,5-bis (trifluoromethyl)benzyl bromide, decafluorobenzhydryl bromide, 2-(perfluorooctyl)ethyl isocyanate, and pentafluorophenyl isocyanate, etc. The silicon compound bound to one terminal end of the block copolymer chain may be chlorine-terminated poly(dimethylsiloxane), or glycidylether-terminated poly(dimethylsiloxane), etc. The halocarbon compound or the silicon compound can be bound to the polymeric chain in the amount of 1 to 50 parts by weight based on 100 parts by weight of total dispersant. When the amount is less than 1 part by weight, the affinity effect for the supercritical fluid by a substituent group cannot be obtained. When the amount exceeds 50 parts by weight, the solubility and dispersion stability to the dispersion solvent are decreased.

Suitable examples of biocides may include both oxidizing biocides and nonoxidizing biocides. Examples of oxidizing biocides may include sodium hypochlorite, hypochlorous acid, chlorine, bromine, chlorine dioxide, and hydrogen peroxide. Examples of non-oxidizing biocides may include aldehydes (such as formaldehyde and glutaraldehyde), quaternary amines, isothizaolines, carbamates, phosphonium quaternary compounds, and halogenated compounds (such as dibromonitrilopropionamide and bromonitropropanediol). Examples of suitable biocides may include those commercially available from Halliburton Energy Services Inc., in Duncan, Okla., under the trade names "ALDACIDE® G," "BE3™," "BE6™," and "BE7™."

The method can further include comparing a plurality of dynamic surface tension measurements of each of the plurality of aqueous test solutions with at least one dynamic surface tension measurement of the aqueous solution to determine the first concentration. As a result of the adsorption of a surfactant at a surface or interface of one or more liquids, a reduction of interfacial tension occurs. Immediately after the surface is produced, the interfacial tension has the same value as the pure liquid(s). The value then reduces until an equilibrium value is reached. With a dynamic tensiometer (e.g. drop volume tensiometer or bubble pressure tensiometer), the size of the interface changes during the measurement. In spite of this, if the change is sufficiently slow, an equilibrium value can often be measured as well as the time-dependent values. In return, the establishment of the equilibrium value with respect to time can also be pursued using static methods in which the size of the interface does not change. The plurality of dynamic surface tension measurements of each of a plurality of aqueous test solutions and the plurality of dynamic surface tension measurements of the aqueous solution can be obtained using any suitable method, including but not limited to the maximum bubble pressure technique specified in ASTM D3825-09, pendant drop method, wihelmy plate method, Langmuir trough method, and combinations thereof. The plurality of dynamic surface tension measurements can be used to create a diffusion profile that is specific to the first component. Subsequently, a dynamic surface tension measurement of a new sample, such as a produced water sample from the head of an oil well can be compared to the diffusion profile to determine the concentration of the first component in the produced water sample. Such measurements can be useful to decide surfactant pumping rate and surfactant performance during and after hydraulic fracturing operations. In addition, these measurements serve a vital role to tailor the surfactant additive to specific reservoir conditions in order to achieve higher oil recovery.

The diffusion profile can include a dynamic surface tension measurement for each of a number of aqueous test solutions. The number of aqueous test solutions can be within a range having a lower limit and/or an upper limit. The range can include or exclude the lower limit and/or the upper limit. The lower limit and/or upper limit can be selected from 1, 5, 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1100, 1200, 1300, 1400, 1500, 1600, 1700, 1800, 1900, 2000, 2100, 2200, 2300, 2400, and 2500. For example, according to certain preferred embodiments, the number of aqueous test solutions can be from 1 to 1000.

According to various embodiments, once the concentration of the first component is determined, the first concentration can be used in a material balance to determine one of the following: a pumping rate of the first component; an amount of the first component in the oil well, surfactants, biocides, scale inhibitors, wax solvents, asphaltenes inhibitors, pour point depressants, demulsifiers, biocides, water clarifiers, shale and clay stabilizers, emulsion breakers, antifoams, scale inhibitors, $H_2S$ and $O_2$ scavengers, corrosion inhibitors, and combinations thereof. The amount of the first component added to the well is known. Once the concentration of the first component in produced water from the well is known, the amount of the first component in the well can be determined using a material balance. Parameters, such as the pumping rate of the first component into the well can be adjusted based on the amount of the first component determined to be in the well compared to the amount of the first component desired in the well. Most surfactants have been deliberately added in a known concentration, for example, at 1000 to 3000 parts per million, to the oil reservoir. If the surfactant is present in the produced water from the oil well, then the surfactant is not doing its job and has no impact on long-term production. Since various embodiments provide a reliable determination of the amount of surfactant coming out of the well, a material balance can be used to determine what is left in the well.

Figure 3:
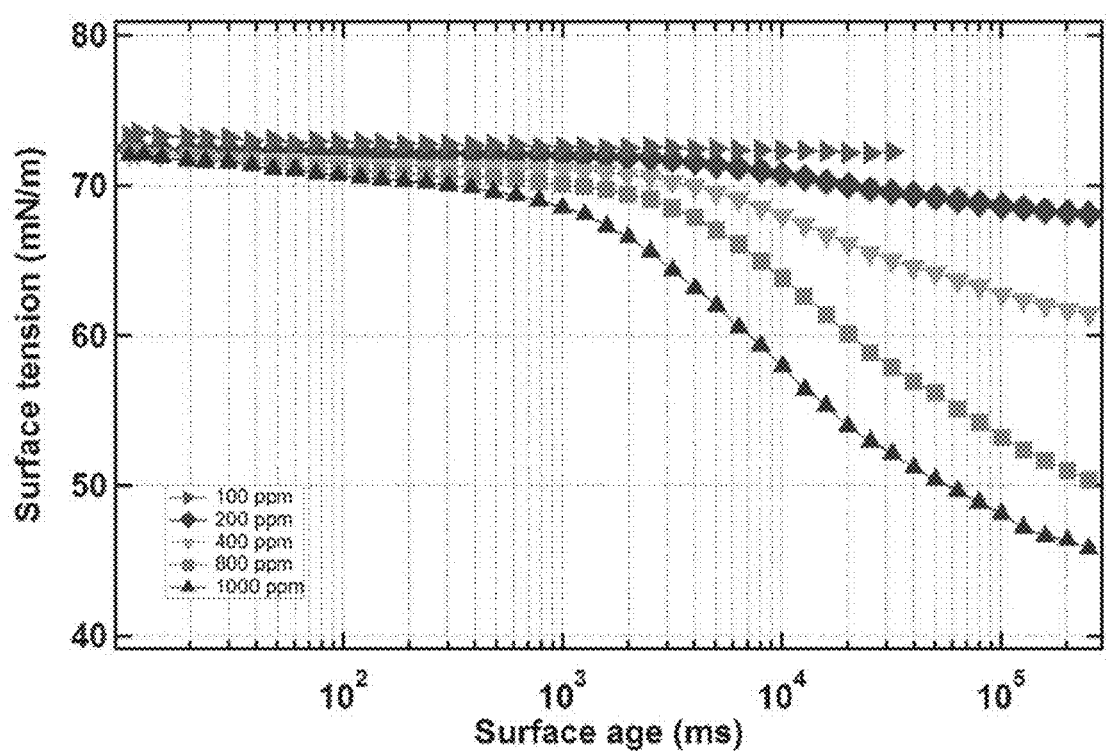
FIG. 3 is a chart showing dynamic surface tension (DST) data for different concentrations of surfactant in DI water.

Various embodiments relate to a method for determining the concentration of a target component in an aqueous sample solution. The method can include identifying an aqueous sample solution including the target component and at least one secondary background component, wherein both the target component and the at least one secondary background component are surface tension altering components; measuring the concentration of the at least one secondary background component; conducting a plurality of dynamic surface tension measurements with an aqueous test solution comprising the at least one secondary background component at the measured concentration and the target component at a plurality of concentrations to obtain a calibrative dynamic surface tension fingerprint of the aqueous test solution as a function of the concentration of the target component; and measuring the dynamic surface tension of the sample aqueous solution and comparing the dynamic surface tension to the calibrative dynamic surface tension fingerprint to obtain the concentration of the target component in the aqueous sample solution. The concentration of surface tension altering compounds in the produced water can change over time. Therefore, it can be beneficial to recreate the calibrative dynamic surface tension fingerprint repeatedly over time. As shown, for example, in FIG. 3, a calibrative dynamic surface tension's fingerprint can be created using dynamic surface tension (DST) measurements of a surfactant at different concentrations in DI water taken over time. In FIG. 3, as the surface age increases, surface tension reduces indicating that surfactant adsorption is occurring on the water-air surface as aging time increases. The slope of DST when plotted against square root of time is equivalent to $4RTC(D/n)^{0.5}$. When this slope is plotted against the bulk concentration of surfactant, it ideally should be a straight line if diffusivity of the monomer concentration is considered. FIG. 4b shows the linear region of slope against the concentration. A straight line fits the data most accurately and shows that the surfactant in the water phase is in a monomeric state and the concentration is still lower than CMC. There is usually a change of slope as the concentration passes through the CMC or nano-aggregation concentration. The range of 100-1000 ppm concentration is selected based on the range of residual surfactant concentration obtained in the produced water. If the DST of an unknown concentration is measured in the range of the calibration curve, the concentration of the surfactant can be estimated. From FIGS. 3 and 4 it can be seen that it is possible to measure an unknown concentration of the surfactant in DI water once the calibration curves are known for DST and UV-Vis.

Figure 11:
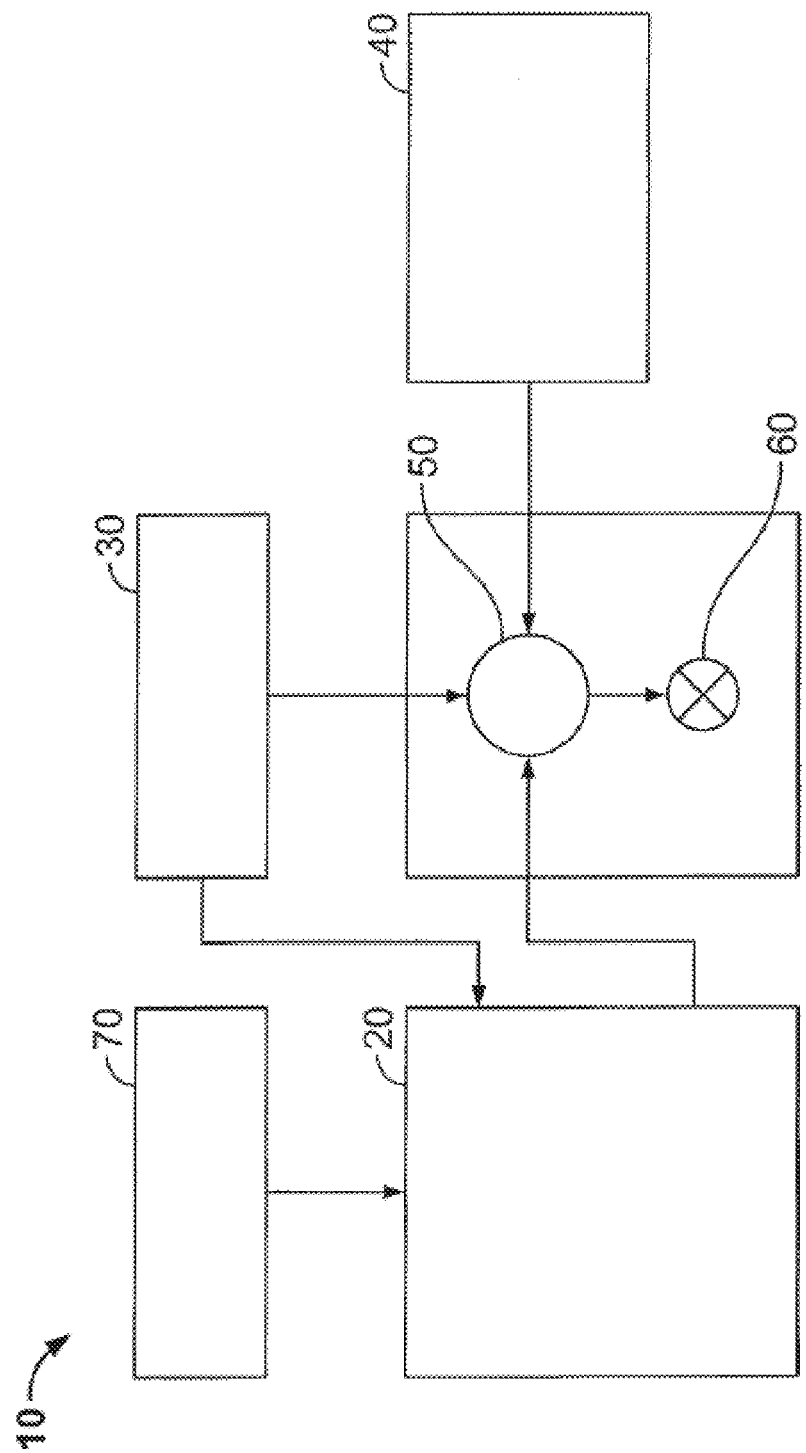
FIG. 11 is a diagram illustrating an example of a fracturing system that may be used in accordance with certain embodiments of the present disclosure.

The exemplary methods and compositions disclosed herein may directly or indirectly affect one or more components or pieces of equipment associated with the preparation, delivery, recapture, recycling, reuse, and/or disposal of the disclosed compositions. For example, and with reference to FIG. 11, the disclosed methods and compositions may directly or indirectly affect one or more components or pieces of equipment associated with an exemplary fracturing system 10, according to one or more embodiments. In certain instances, the system 10 includes a fracturing fluid producing apparatus 20, a fluid source 30, a proppant source 40, and a pump and blender system 50 and resides at the surface at a well site where a well 60 is located. In certain instances, the fracturing fluid producing apparatus 20 combines a gel pre-cursor with fluid (e.g., liquid or substantially liquid) from fluid source 30, to produce a hydrated fracturing fluid that is used to fracture the formation. The hydrated fracturing fluid can be a fluid for ready use in a fracture stimulation treatment of the well 60 or a concentrate to which additional fluid is added prior to use in a fracture stimulation of the well 60. In other instances, the fracturing fluid producing apparatus 20 can be omitted and the fracturing fluid sourced directly from the fluid source 30. In certain instances, the fracturing fluid may comprise water, a hydrocarbon fluid, a polymer gel, foam, air, we gases and/or other fluids.

The proppant source 40 can include a proppant for combination with the fracturing fluid. The system may also include additive source 70 that provides one or more additives (e.g., gelling agents, weighting agents, and/or other optional additives) to alter the properties of the fracturing fluid. For example, the other additives 70 can be included to reduce pumping friction, to reduce or eliminate the fluid's reaction to the geological formation in which the well is formed, to operate as surfactants, and/or to serve other functions.

The pump and blender system 50 receives the fracturing fluid and combines it with other components, including proppant from the proppant source 40 and/or additional fluid from the additives 70. The resulting mixture may be pumped down the well 60 under a pressure sufficient to create or enhance one or more fractures in a subterranean zone, for example, to stimulate production of fluids from the zone. Notably, in certain instances, the fracturing fluid producing apparatus 20, fluid source 30, and/or proppant source 40 may be equipped with one or more metering devices (not shown) to control the flow of fluids, proppants, and/or other compositions to the pumping and blender system 50. Such metering devices may permit the pumping and blender system 50 can source from one, some or all of the different sources at a given time, and may facilitate the preparation of fracturing fluids in accordance with the present disclosure using continuous mixing or "on-the-fly" methods. Thus, for example, the pumping and blender system 50 can provide just fracturing fluid into the well at some times, just proppants at other times, and combinations of those components at yet other times.

Figure 12:
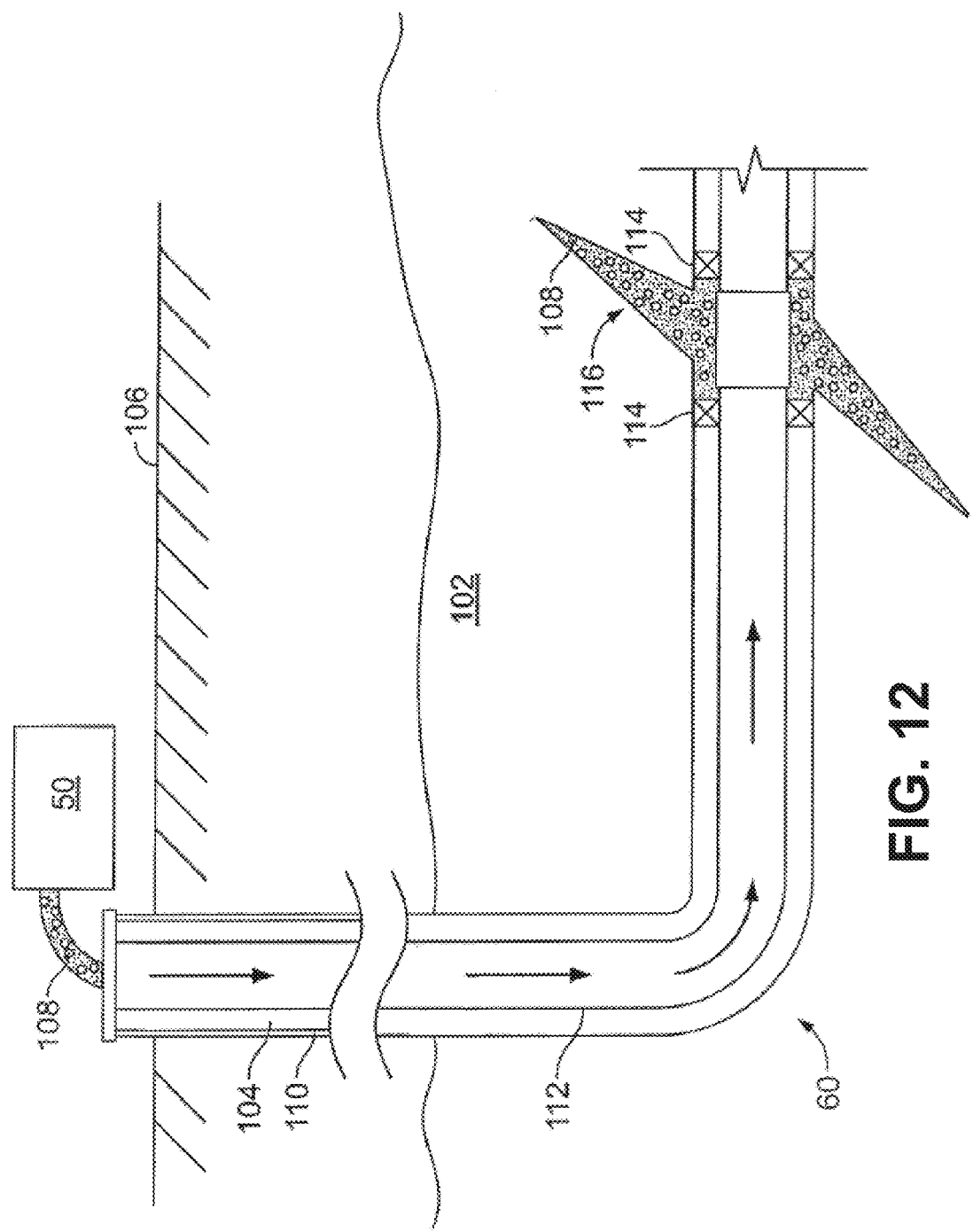
FIG. 12 is a diagram illustrating an example of a subterranean formation in which a fracturing operation may be performed in accordance with certain embodiments of the present disclosure.

FIG. 12 shows the well 60 during a fracturing operation in a portion of a subterranean formation of interest 102 surrounding a well bore 104. The well bore 104 extends from the surface 106, and the fracturing fluid 108 is applied to a portion of the subterranean formation 102 surrounding the horizontal portion of the well bore. Although shown as vertical deviating to horizontal, the well bore 104 may include horizontal, vertical, slant, curved, and other types of well bore geometries and orientations, and the fracturing treatment may be applied to a subterranean zone surrounding any portion of the well bore. The well bore 104 can include a casing 110 that is cemented or otherwise secured to the well bore wall. The well bore 104 can be uncased or include uncased sections. Perforations can be formed in the casing 110 to allow fracturing fluids and/or other materials to flow into the subterranean formation 102. In cased wells, perforations can be formed using shape charges, a perforating gun, hydro-jetting and/or other tools.

The well is shown with a work string 112 depending from the surface 106 into the well bore 104. The pump and blender system 50 is coupled a work string 112 to pump the fracturing fluid 108 into the well bore 104. The working string 112 may include coiled tubing, jointed pipe, and/or other structures that allow fluid to flow into the well bore 104. The working string 112 can include flow control devices, bypass valves, ports, and or other tools or well devices that control a flow of fluid from the interior of the working string 112 into the subterranean zone 102. For example, the working string 112 may include ports adjacent the well bore wall to communicate the fracturing fluid 108 directly into the subterranean formation 102, and/or the working string 112 may include ports that are spaced apart from the well bore wall to communicate the fracturing fluid 108 into an annulus in the well bore between the working string 112 and the well bore wall.

The working string 112 and/or the well bore 104 may include one or more sets of packers 114 that seal the annulus between the working string 112 and well bore 104 to define an interval of the well bore 104 into which the fracturing fluid 108 will be pumped. FIG. 12 shows two packers 114, one defining an uphole boundary of the interval and one defining the downhole end of the interval. When the fracturing fluid 108 is introduced into well bore 104 (e.g., in FIG. 12, the area of the well bore 104 between packers 114) at a sufficient hydraulic pressure, one or more fractures 116 may be created in the subterranean zone 102. The proppant particulates in the fracturing fluid 108 may enter the fractures 116 where they may remain after the fracturing fluid flows out of the well bore. These proppant particulates may "prop" fractures 116 such that fluids may flow more freely through the fractures 116.

While not specifically illustrated herein, the disclosed methods and compositions may also directly or indirectly affect any transport or delivery equipment used to convey the compositions to the fracturing system 10 such as, for example, any transport vessels, conduits, pipelines, trucks, tubulars, and/or pipes used to fluidically move the compositions from one location to another, any pumps, compressors, or motors used to drive the compositions into motion, any valves or related joints used to regulate the pressure or flow rate of the compositions, and any sensors (i.e., pressure and temperature), gauges, and/or combinations thereof, and the like.

EXAMPLES

Residual surfactant concentration was measured in the produced water from various wells from the Barnett using the dynamic surface tension technique, according to various embodiments, which allows for accurate measurements. Comparison of dynamic surface tension is actually comparing diffusion coefficient and reaction kinetics of adsorption of one or more known molecules in the produced water. Short time kinetics of adsorption of different molecules is different based on their chemical nature and molecular size. UV-Vis spectroscopy is used to confirm the results. An estimate of residual concentrations from UV-Vis seems to be coherent with dynamic surface tension measurement value.

Such measurements can be useful to decide surfactant pumping rate and surfactant performance during and after hydraulic fracturing operations. In addition, these measurements serve a vital role to tailor the surfactant additive to specific reservoir conditions in order to achieve higher oil recovery. Real time production results from those different wells are analyzed and seem to be dependent on the corresponding residual surfactant concentrations from the produced waters. This unique technique is used for the first time to study and analyze the produced water for surfactant additive concentration.

The examples provided herein measure residual surfactant concentration by measuring the dynamic surface tension of produced water. Measuring residual surfactant in the produced water can be extremely useful to understand the performance of the surfactant in the field. Real time measurement of such quantity in the flowback can even help us understand the how much of surfactant is getting used and if we need to add more or less during pumping in future timeframe.

Because of the presence of various total dissolved solids (TDS) levels and other fracturing additives such as friction reducers, scale inhibitors or biocides, it is not an easy task to track surfactant residuals. Conventional methods such as methylene blue (MB) based absorbance measurements take into account the bonding between anionic surfactants and cationic MB, but MB would bond with anything that is anionic in produced waters, resulting in erroneous analysis. Therefore, following the conventional dye based approach, such as methylene blue that typically combines with anionic surfactants, it is required that the concentration of the combined complex be determined by using spectroscopic methods. This approach, however, can lead to erroneous results because of the presence of anionic friction reducers, scale inhibitor or gelled fluids.

Surfactants have a unique property to diffuse to the interface as soon as it is created. Making use of this property, dynamic surface tension of surfactant containing fluid is measured by using bubble pressure technique. As surface age of the bubble increases, more surfactant adsorb at the surface causing surface tension to drop. For short times, there are no molecules of surfactants at the surface once the surface is created and excess molecules of surfactants in the bulk phase. Therefore, concentration gradient i.e. diffusion drives the surfactant adsorption at short times. The adsorption can be explained by the Ward-Tordai equation which considers process to be diffusion controlled. For short times:

$$\gamma_{t\to 0} = \gamma_0 - 4RTC\left(\frac{Dt}{\pi}\right)^{1/2} \qquad \text{Eq. 1}$$

The parameters C, $\gamma$, $\gamma_0$ and D are bulk concentration of surfactant monomers, surface tension, surface tension of pure solvent and diffusion coefficient of monomer concentration respectively. Diffusivity of a molecule is a unique property for a solute solvent system. Once diffusivity is known concentration can be estimated with the equation mentioned above. Of course, surfactant that has been used in the field is not just one molecule-it's actually a mixture of different chemicals. Hence, the effective diffusivity of the surfactant in the solvent (or produced water) is first estimated to estimate the concentration.

Figure 2:
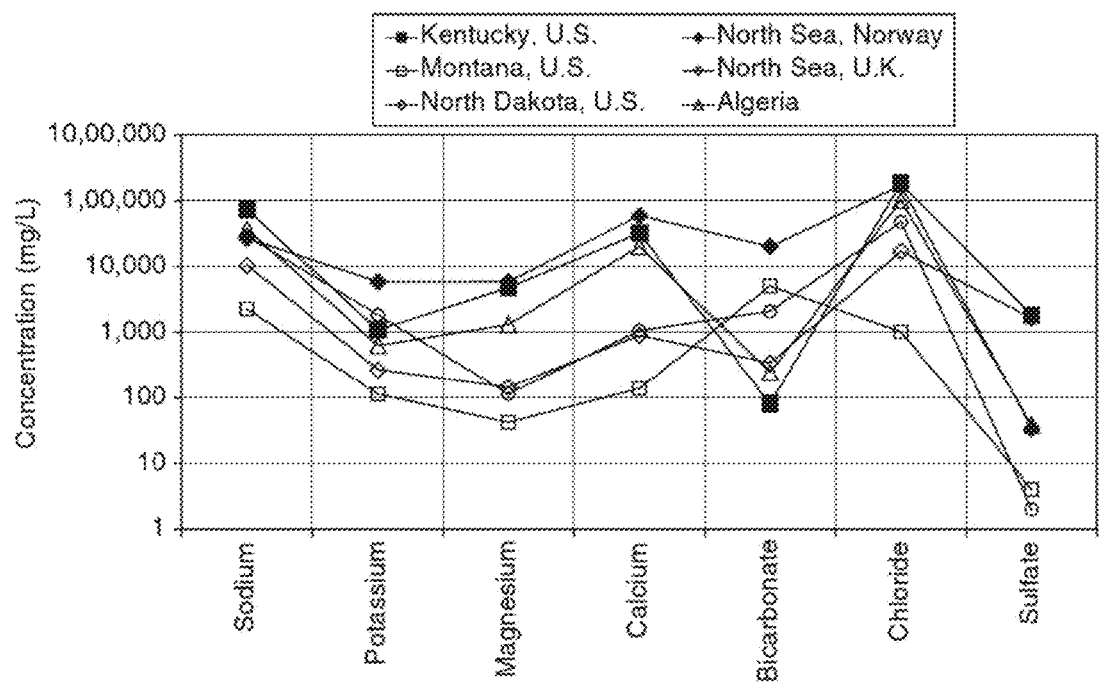
FIG. 2 is a chart showing ionic concentrations of various formation waters of oil fields from various parts of the world.

TDS affects diffusivity of surfactant molecule in the bulk phase. It has been studied and recognized that surface tension depends and diffusivity of surfactant depends upon the TDS of the produced water. It is important to know the water analysis of produced water to understand which salts and ions are present in the produced water which might affect the diffusivity of the surfactant. For different wells, concentration of different ions differs significantly. FIG. 2 is a chart showing ionic concentrations of various formation waters of oil fields from various parts of the world. As seen from FIG. 2, the diffusivity of the surfactant can differ by an order of magnitudes from well to well.

Measurement of effective diffusivity of a surfactant in particular brine from short time Ward-Tordai equation enable us to measure the concentration of unknown surfactant concentration in the same solvent phase. Measurements from UV-Vis spectra confirm the estimation from DST measurements.

Example 1

A purpose of this example was to determine the concentration of surfactant in DI water. DI water was used to demonstrate an estimation of an equivalent diffusion coefficient. FIG. 3 shows the dynamic surface tension (DST) of surfactant at different concentration in DI water. As surface age increases, surface tension reduces indicating that surfactant adsorption on the water-air surface as aging time increases.

At short times, from Equation 1, the slope of DST when plotted against square root of time is equivalent to $4RTC(D/n)^{0.5}$. When this slope is plotted against the bulk concentration of surfactant, it ideally should be a straight line if diffusivity of monomer concentration is considered. FIG. 4b shows the linear region of slope against the concentration. Straight line fits the data almost accurately showing that the surfactant in water phase is in monomeric state and concentration is still lower than CMC. There is usually a change of slope as concentration passes through the CMC or nano-aggregation concentration. The range of concentration 100-

1000 ppm is selected based on the range of residual surfactant concentration obtained in the produced water. The effective diffusivity of the surfactant is $3.92 \times 10^{-8}$ m$^2$/s from Eq. 1 and FIG. 4. Hence, if the DST of unknown concentration is measured in the range of the calibration curve, the concentration of the surfactant can be estimated.

Figure 4A:
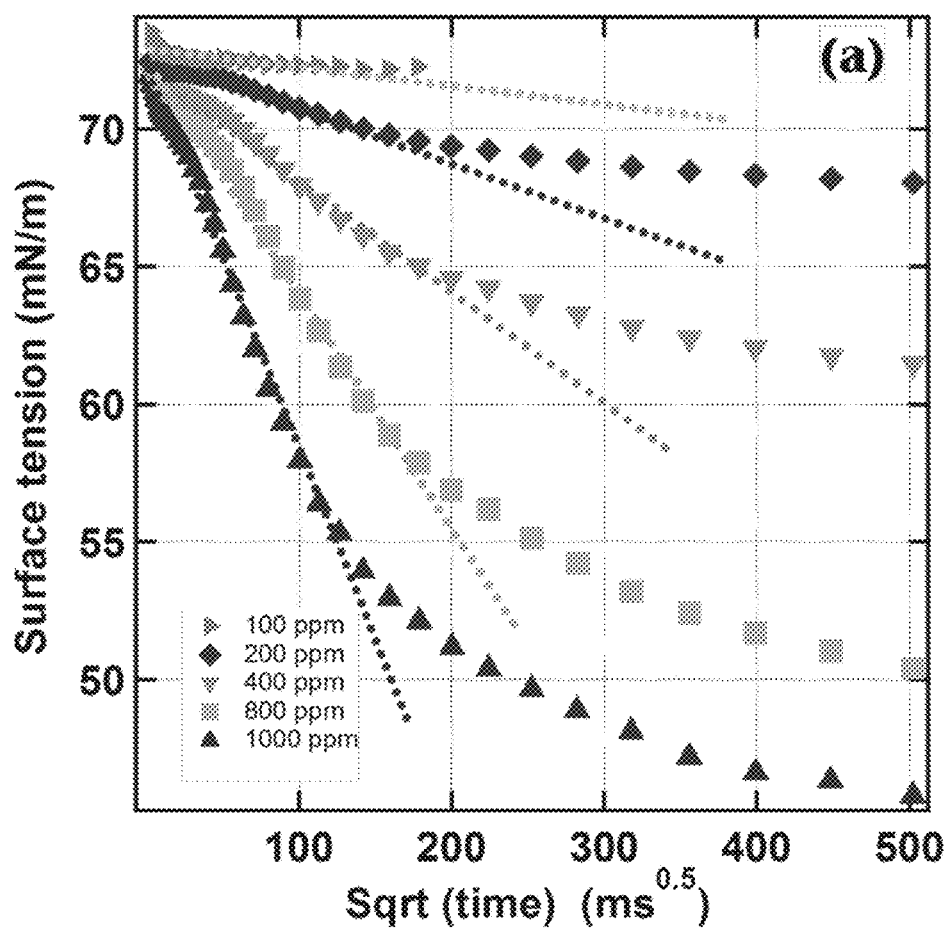
FIG. 4 ($a$) is a chart showing surface tension plotted against square root of time showing initial linear region of short times kinetics.
Figure 4B:
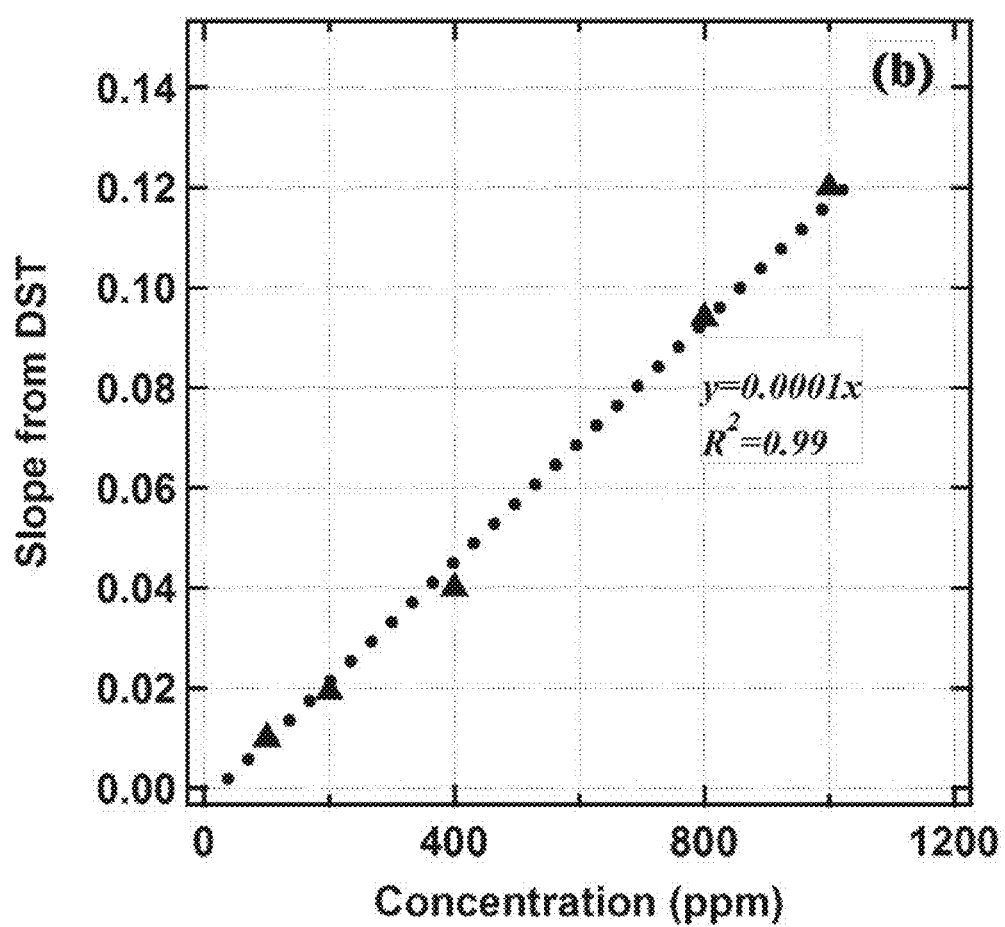
Figure 5A:
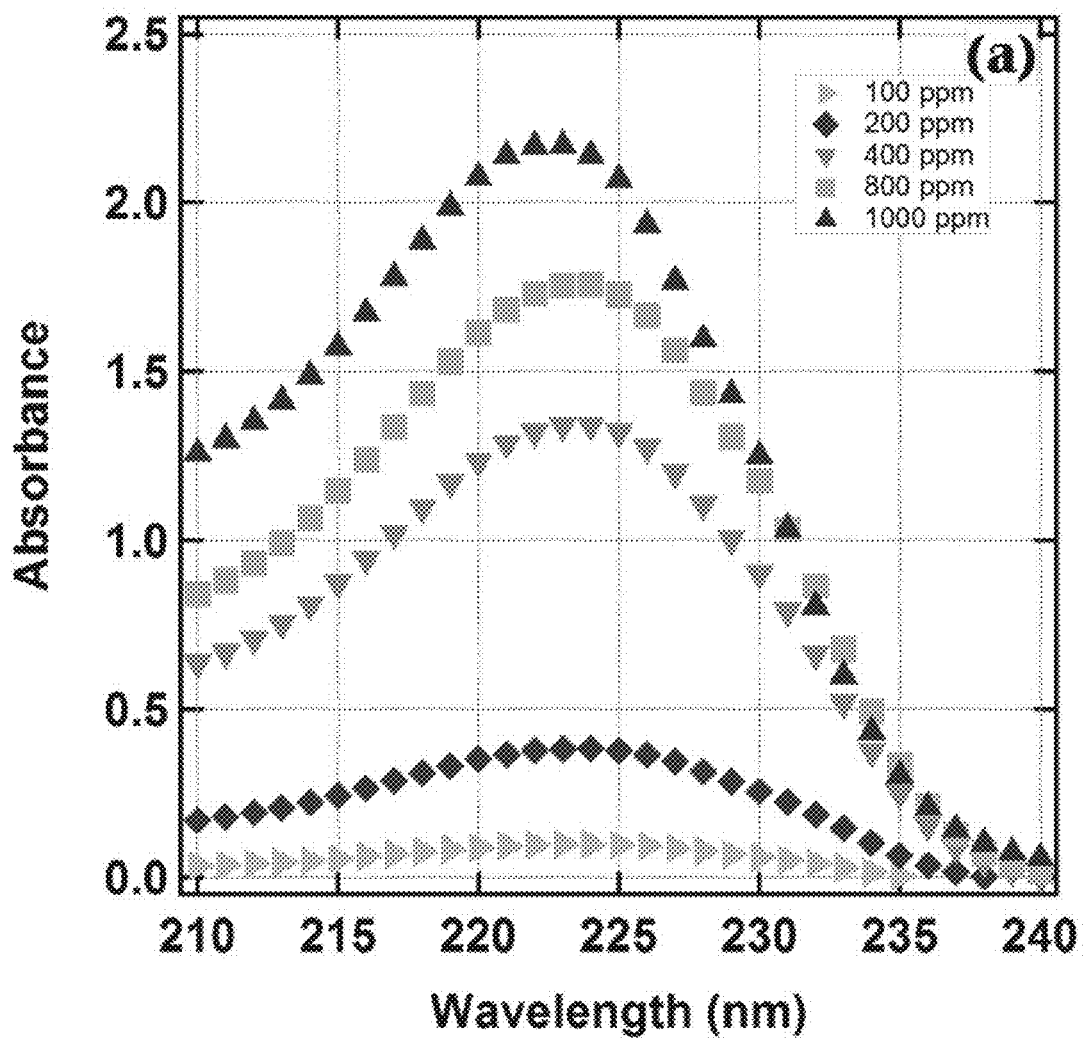
FIG. 5($a$) is a chart showing UV-visible data of surfactant in DI water from 210-240 nm wavelengths.
Figure 5B:
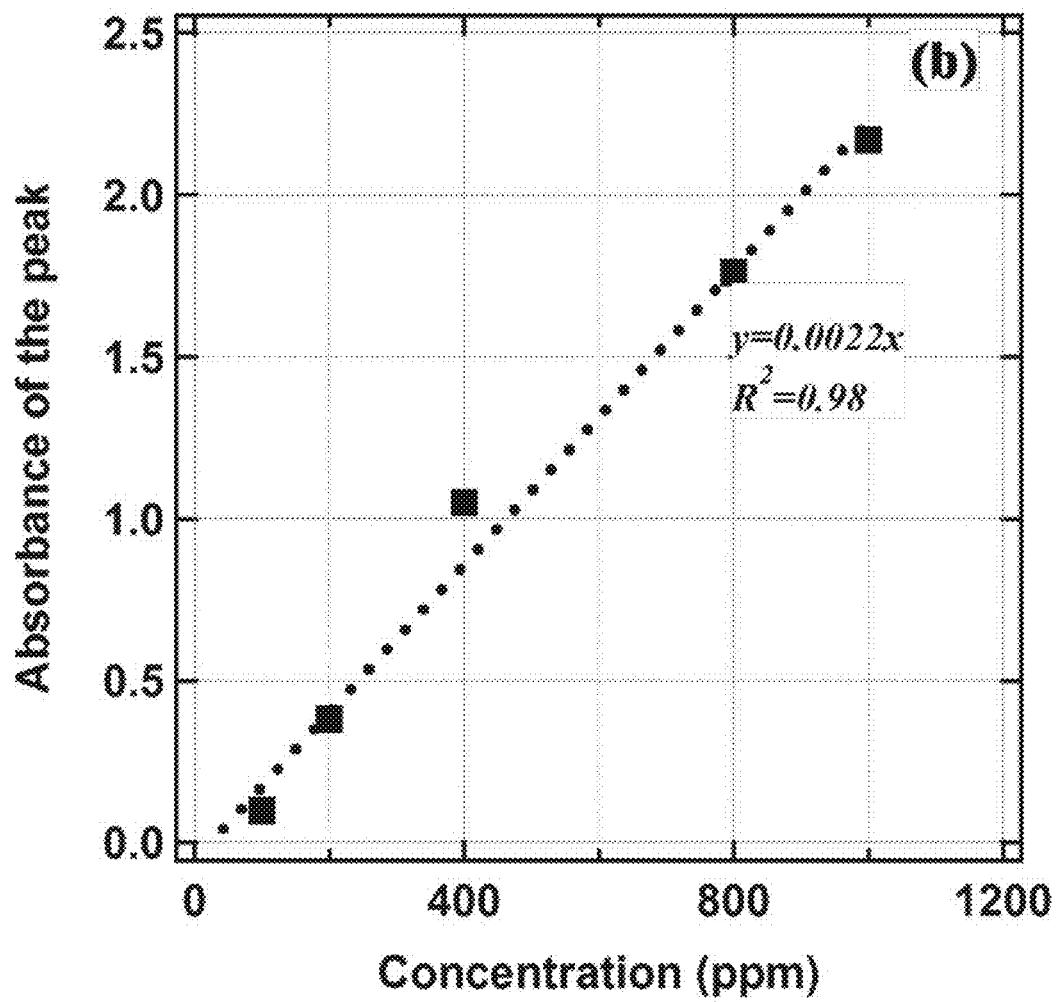

From FIGS. 3 and 4 it can be seen that, it is possible to measure unknown concentration of the surfactant in DI water once the calibration curves are known for DST and UV-Vis. To confirm this calibration curve over the concentration range, UV-vis spectroscopy is used. As shown in FIG. 5, one of the main ingredients in the surfactant gives a molecular absorption peak around 215-235 nm, as the molecular concentration increases absorption increases. For the same range of concentrations, the calibration curve is plotted, which shows an extremely good fit to the data.

Figure 6A:
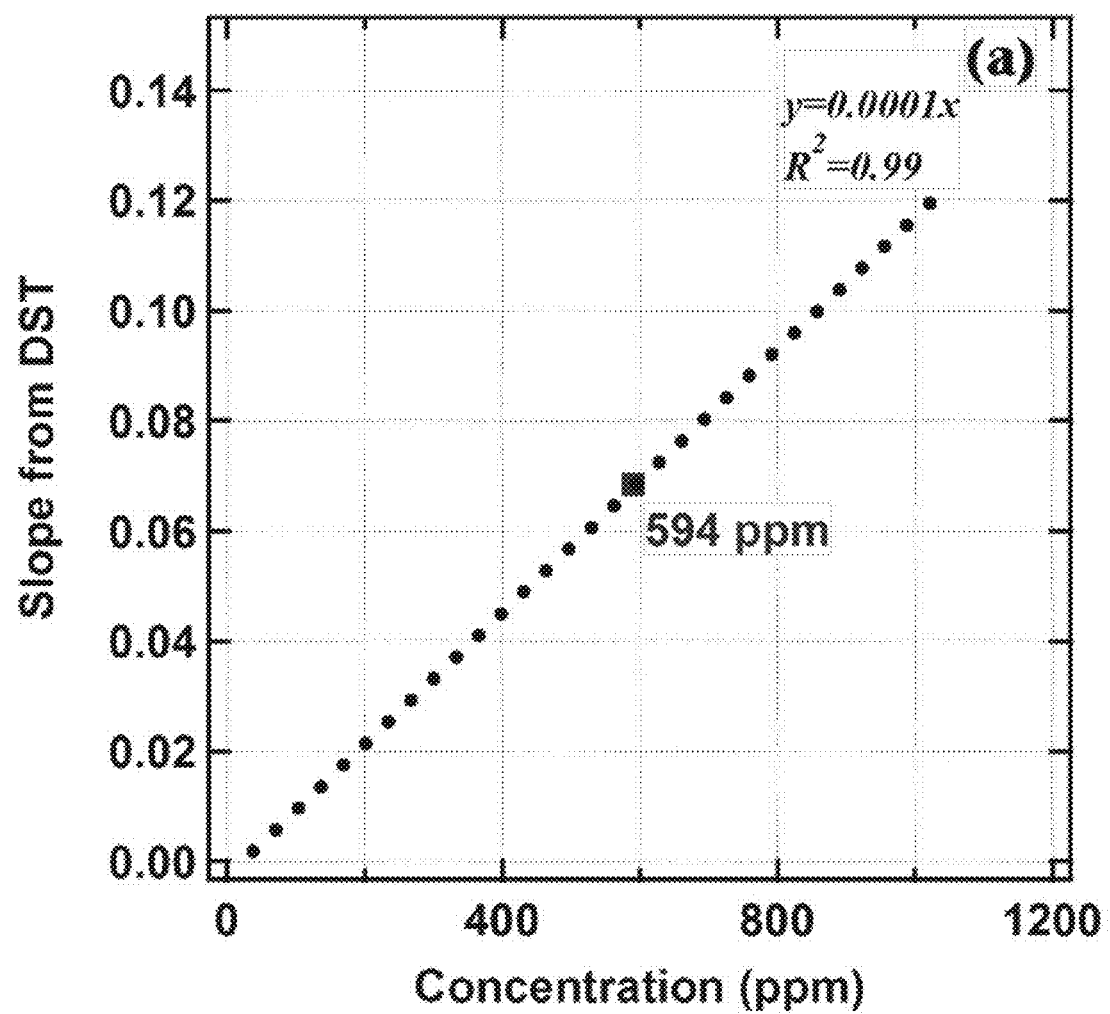
FIG. 6 ($a$) is a chart showing a prediction of about 600 ppm (594 ppm) surfactant concentration from an exemplary DST calibration curve.
Figure 6B:
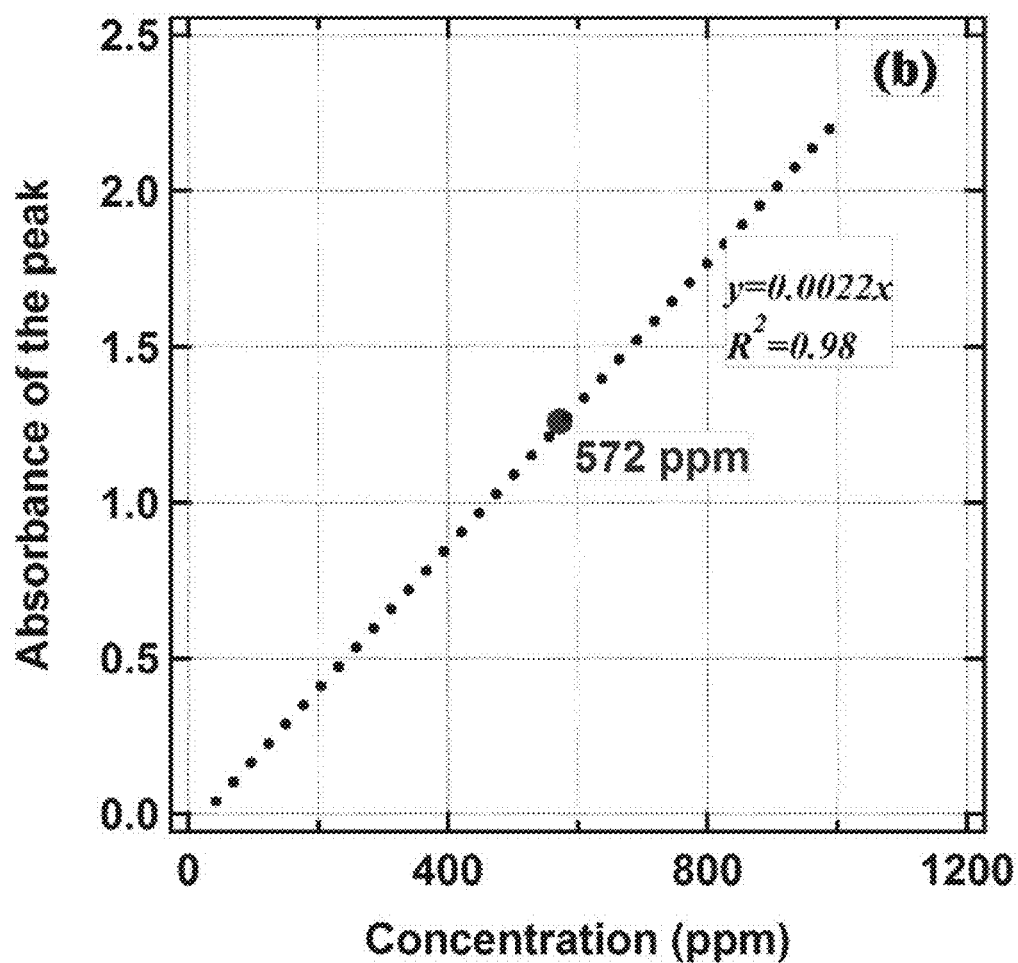

A sample of 600 ppm surfactant was prepared and from DST and UV-vis spectroscopy the concentration was estimated. As seen from FIG. 6, it is seen that DST and UV-vis predictions are closer to actual value of the concentration. Prediction from DST seems to be closer to the actual value. Therefore, DST measurement can be utilized for concentration prediction.

Example 2

A purpose of this example was to determine the concentration of residual surfactant in produced water from an oil well. As mentioned in introduction to the Examples, different produced waters have different TDS. Hence, interaction of surfactant in the bulk phase changes affecting its diffusivity. Therefore, it is mandatory to match the TDS of produced water to a calibration curve. From water analysis of one of the wells from Barnett, synthetic brine was prepared. Analysis of the water is shown below in Table 1, which shows formation water analyses from ion exchange chromatography.

TABLE 1

Analysis @ Properties in Sample Specifics

| Cations | mg/L | Anions | mg/L |
| --- | --- | --- | --- |
| Sodium (Na): | 22402.63 | Chloride (Cl): | 38000.00 |
| Potassium (K): | 75.98 | Sulfate (SO$_4$) | 152.00 |
| Magnesium (Mg): | 303.27 | Bicarbonate (HCO$_3$) | 1464.00 |
| Calcium (Ca): | 1765.43 | Carbonate (CO$_3$) | |
| Strontium (Sr): | 345.09 | Acetic Acid (CH$_3$COO) | |
| Barium (Ba): | 10.86 | Propionic Acid (C$_2$H$_5$COO) | |
| Iron (Fe): | 40.09 | Butanoic Acid (C$_3$H$_7$COO) | |
| Zinc (Zn): | 0.10 | Isobutyric Acid ((CH$_3$)$_2$CHCOO) | |
| Lead (Pb): | 0.13 | Fluoride (F): | |
| Ammonia NH$_3$ | | Bromine (Br): | |
| Manganese (Mn): | 1.82 | Silica (SiO$_2$) | |

Figure 7:
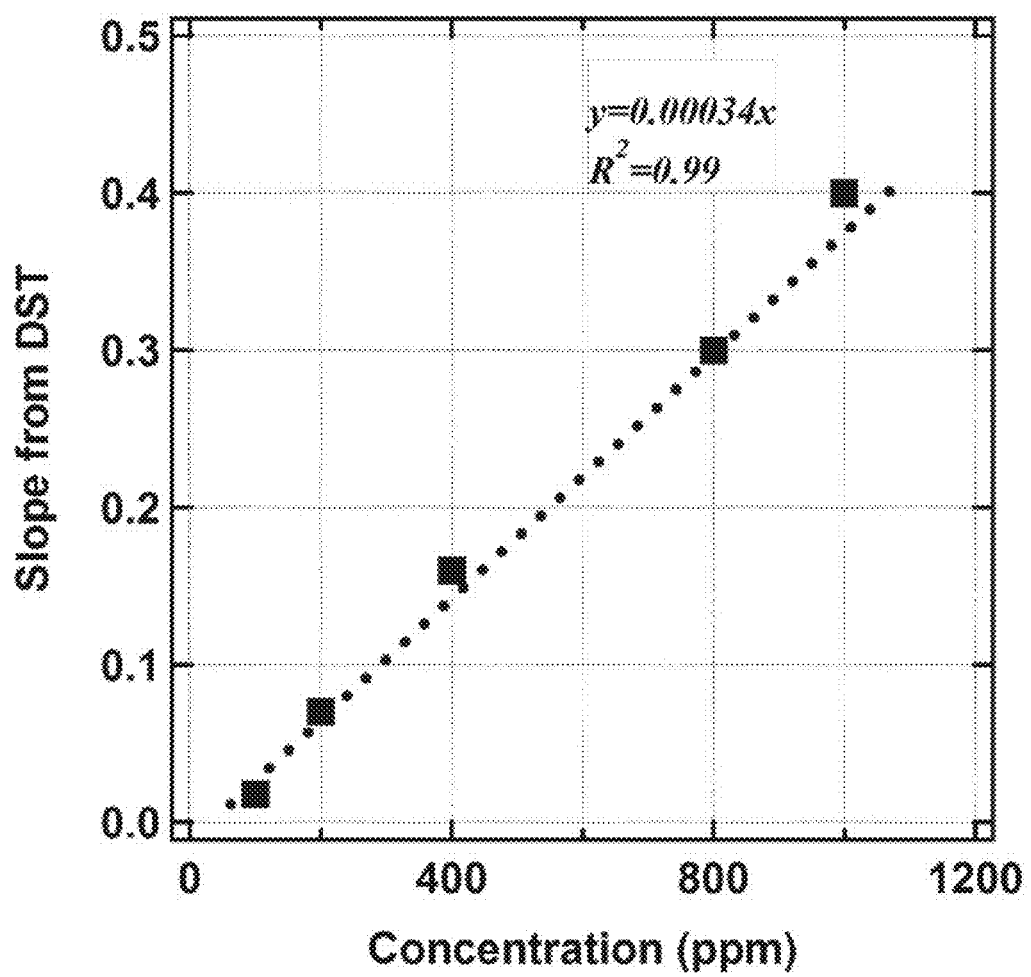
FIG. 7 is a chart showing a calibration curve of the slope from DST of different surfactant concentrations in synthetic brine against concentration of surfactant.

Synthetic brine was prepared to these specific ionic concentrations of different salts. DST was measured for different concentrations to build a calibration curve shown in FIG. 7. FIG. 7 shows the slope from DST of different surfactant concentrations in synthetic brine against concentration of surfactant. The slope of this curve is almost three times as it was for DI water. Therefore, it seems that surface tension drop and diffusivity increase with increase in TDS of the produced water.

Example 3

Figure 8A:
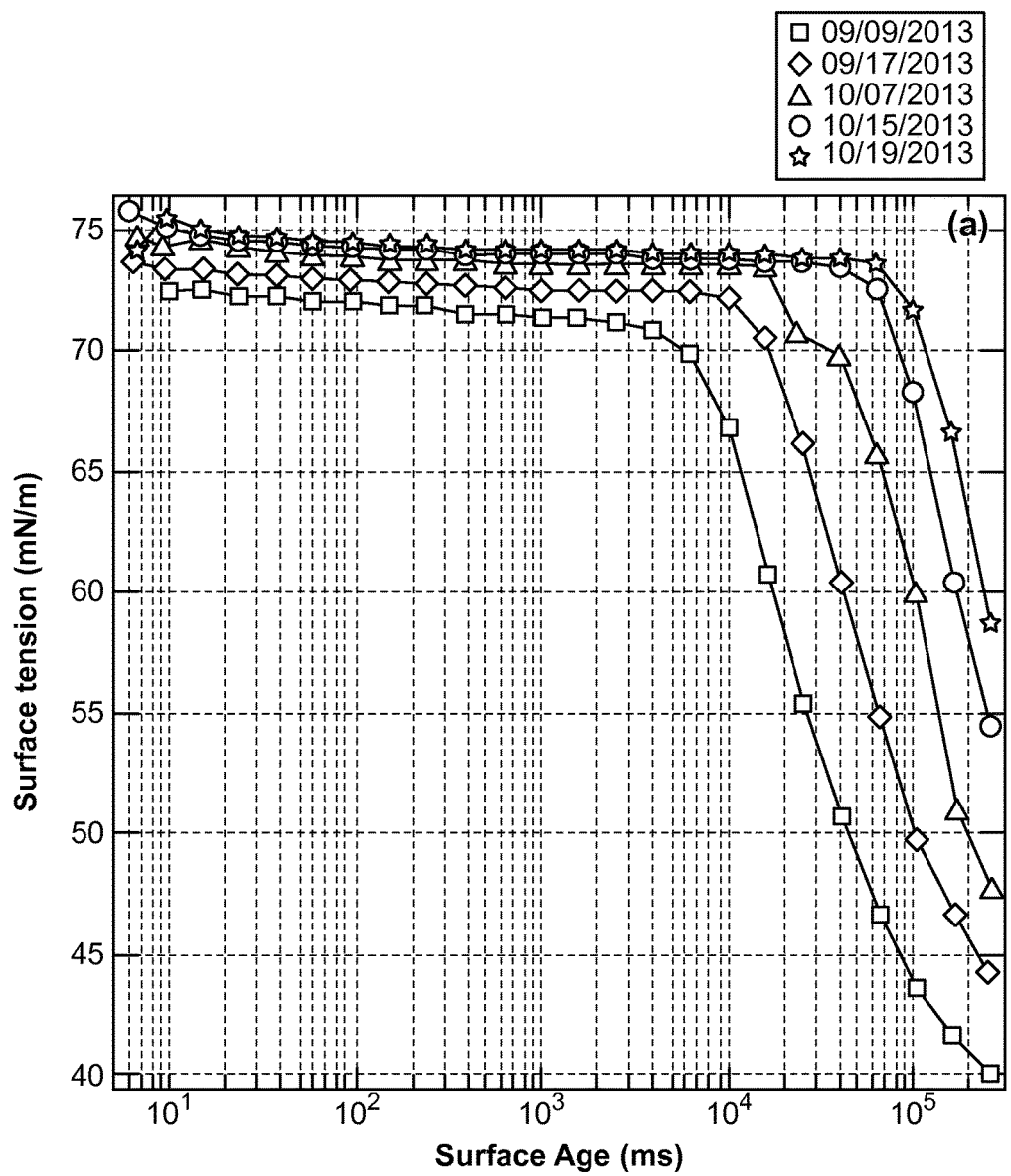
FIG. 8($a$) is a chart showing DST of produced water at different days.
Figure 8B:
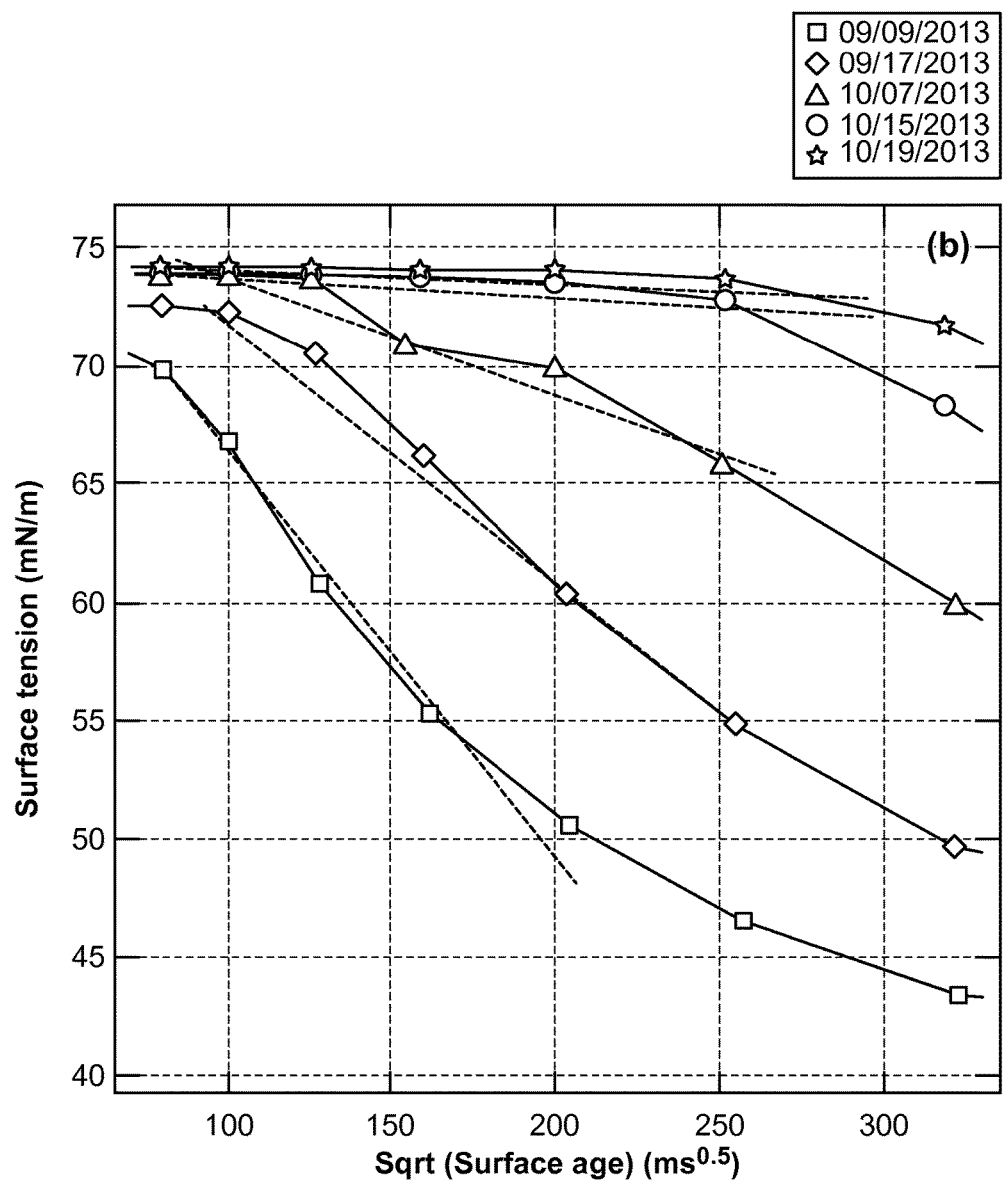

A purpose of this example is to demonstrate real time production data and residual surfactant concentration. For these Barnett wells, 3 gpt of the surfactant was injected into the well with fracturing fluid. After measuring calibration curve in the synthetic brine, DST of produced water samples from the field is measured as they are received after every few days. DST data of different samples received at different dates are shown in FIG. 8. For the short time slope, DST is plotted against the square root of time. FIG. 8 (a) is a chart showing DST of produced water at different days. FIG. 8(b) is a chart showing surface tension against square root of time for the same.

Figure 9:
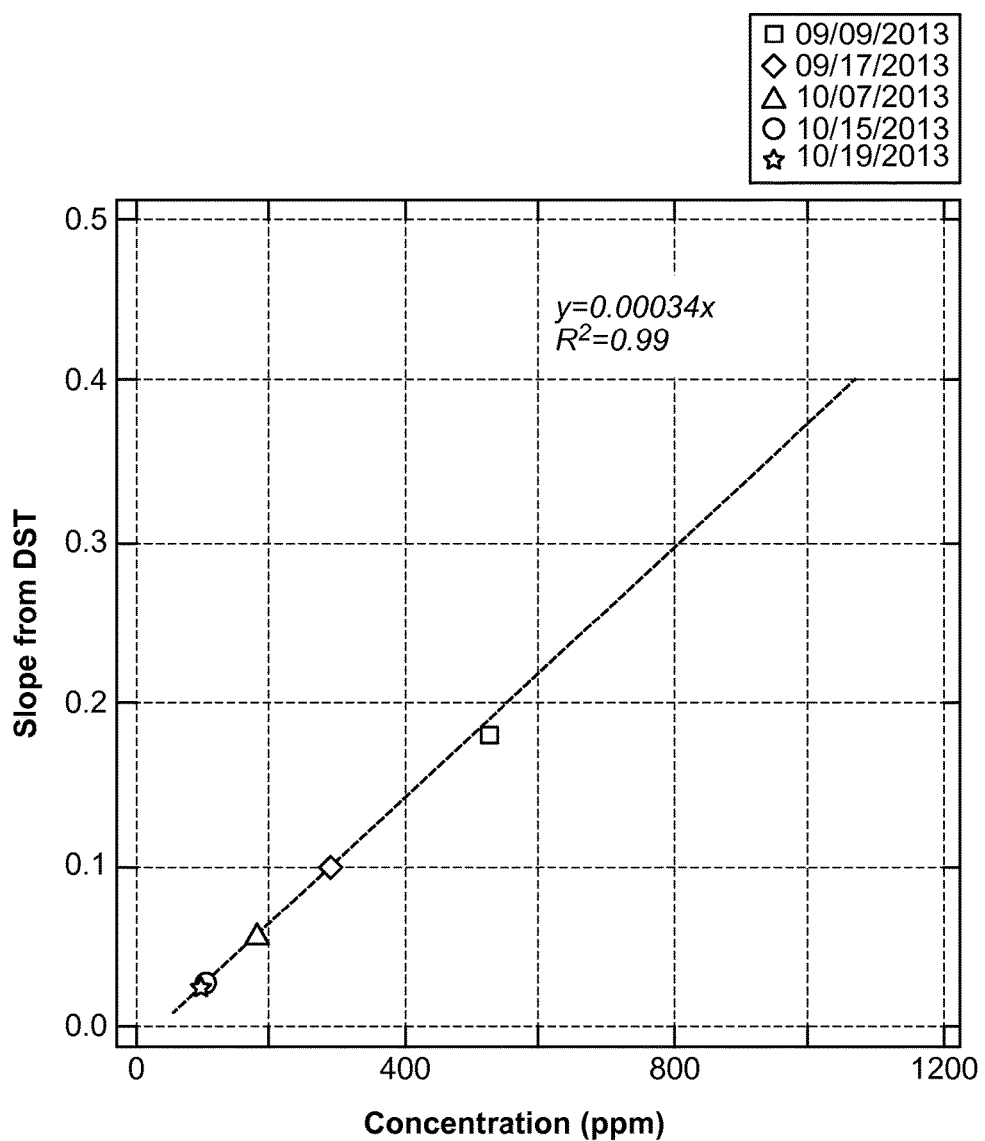
FIG. 9 is a chart showing a prediction of residual concentration of surfactant in produced water from calibration curve.

From the calibration curve, the residual concentration of produced water can be estimated as shown in FIG. 9. More specifically, FIG. 9 provides a prediction of residual concentration of surfactant in produced water from calibration curve.

Figure 10:
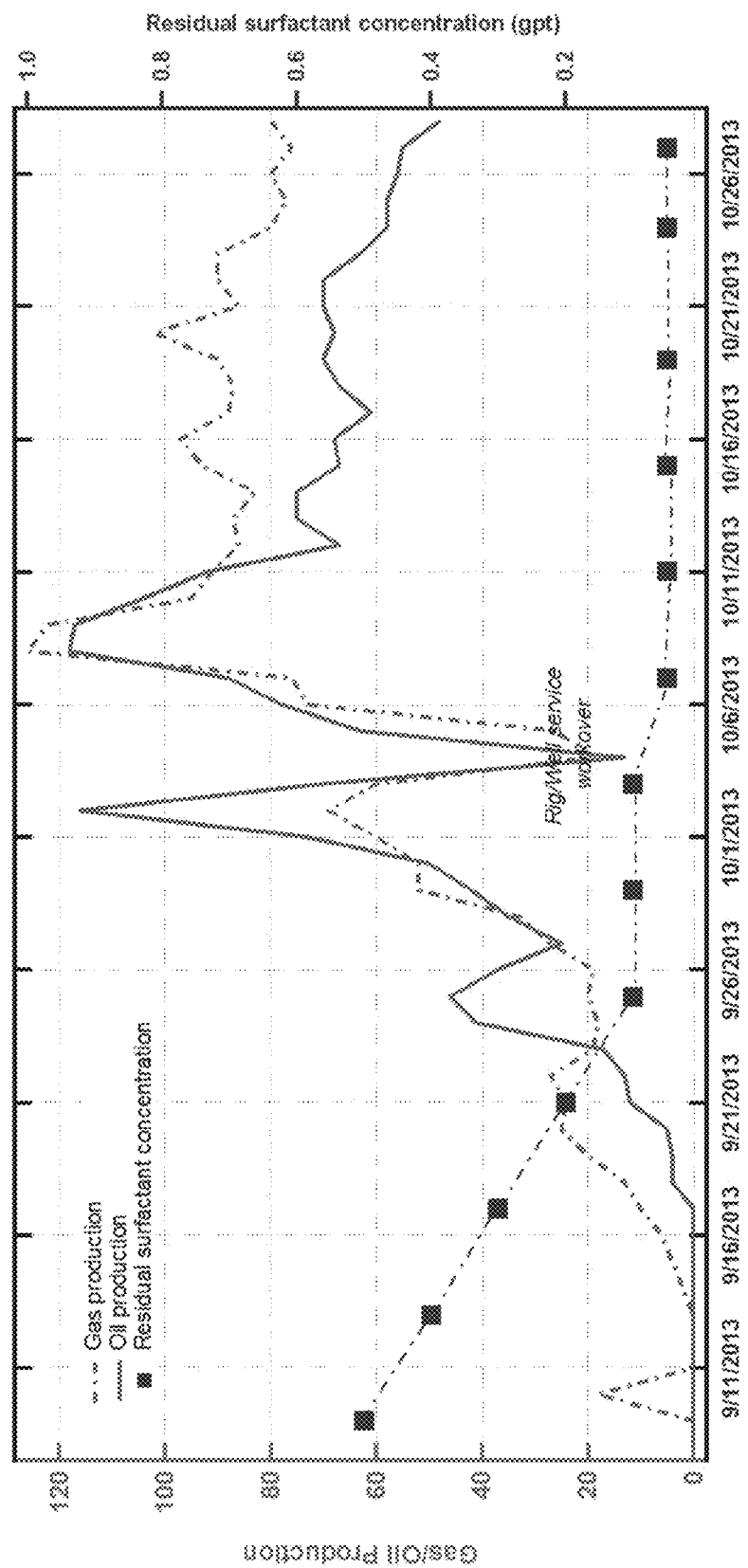
FIG. 10 is a chart showing real time production data of oil and gas with residual surfactant concentration in produced water samples.

Similarly, for different produced water samples collected at different days of flow back, we measure DST and predict the residual concentration of surfactant. FIG. 10 shows the real time oil and gas production data with residual surfactant concentration in the flow back water.

It is seen that as time progresses, concentration of surfactant in produced water decreases. This observation is coherent with the fact that more the aging time given to surfactants downhole, more it will adsorb on oil and rock surfaces downhole. Real time surfactant utilization can be estimated from such measurements. On Sep. 9, 2013, utilization of surfactant was around 83%, indicating that 83% of injected surfactant was being utilized in the well. By the end of Oct. 26, 2013, utilization of surfactant increased to 98%. With increasing adsorption of surfactant in downhole conditions, more oil and gas production is seen from the real time production data. Such data indicates that the surfactants effectively adsorb on oil surfaces to mobilize it forming weak emulsions and bringing it to the surface.

Based on Examples 1-3, initial adsorption kinetics from dynamic surface tension data is diffusion limited. By using the Ward Tordai equation for short times, unique linear curve of slope of concentration against square root of time against concentration can be obtained. The slope of such curve is a diffusivity equivalent and follows extremely good linear fit. Hence, by measuring DST of unknown concentration of surfactant we can estimate the concentration from such calibration curve. The estimate from DST is very accurate and is coherent with UV-Vis measurement.

The diffusivity equivalent slope is sensitive to TDS of the water. Synthetic brine is prepared from the water analysis of produced well and calibration curve is obtained. Such calibration curve is used to estimate concentration of residual surfactant in produced water.

Real time field data suggests that surfactant utilization increases with aging time. It is seen from the data that as surfactant utilization increases oil-gas production increases.

Although the present disclosure has been described in considerable detail with reference to certain preferred versions thereof, other versions are possible. Therefore, the spirit and scope of the appended claims should not be limited to the description of the preferred versions contained herein.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Regarding the several embodiments described and claimed herein concerning the concentration determination of constituent components of aqueous solutions, it is further disclosed in association therewith that the ionic surfactant can be a cationic surfactant selected from the group consisting of alkyltrimethylammonium salts, dialkyldimethylammonium salts, alkyldimethylbenzylammonium salts, alkylpyridinium salts, alkylisoquinolinium salts, benzethonium chloride, and acylamino acid type cationic surfactants, and combinations thereof. Furthermore, the first component can be an amphoteric surfactant selected from the group consisting of an amino acid, betaine, sultaine, phosphobetaines, imidazoline type amphoteric surfactants, soybean phospholipid, and yolk lecithin. Examples for amphoteric surfactants are, but not limited to, sodium N-dodecyl-beta-alanine, sodium N-lauryl-beta-iminodipropionate, myristoamphoacetate, lauryl betaine, and laurylsulfobetaine, and combinations thereof. Still further, the first component can be an oil field chemical selected from the group consisting of production chemicals, frack additives, surfactants, biocides, scale inhibitors, wax solvents, asphaltenes inhibitors, pour point depressants, biocides, water clarifiers, shale and clay stabilizers, emulsion breakers, antifoams, scale inhibitors, $H_2S$ and $O_2$ scavengers, corrosion inhibitors, and combinations thereof. In another aspect, the plurality of dynamic surface tension measurements of each of a plurality of aqueous test solutions and the plurality of dynamic surface tension measurements of the aqueous solution can be obtained using one of the following: the maximum bubble pressure technique, the pendant drop technique, the Wihelmy plate technique, the Langmuir trough technique, and combinations thereof.

Any element in a claim that does not explicitly state "means for" performing a specified function, or "step for" performing a specific function, is not to be interpreted as a "means" or "step" clause as specified in 35 U.S.C § 112, sixth paragraph. In particular, the use of "step of" in the claims herein is not intended to invoke the provisions of 35 U.S.C § 112, sixth paragraph.

What is claimed is:

1. A method comprising:
   obtaining a first aqueous sample from a well;
   identifying a background component that alters a surface tension of the first aqueous sample;
   measuring a concentration of the background component of the first aqueous sample;
   creating a synthetic aqueous solution comprising the background component at the measured concentration;
   conducting a plurality of dynamic surface tension measurements with the synthetic aqueous solution comprising a target component at a plurality of pre-determined concentrations;
   obtaining calibrative dynamic surface tension curves of the synthetic aqueous solution as a function of the concentration of the target component based on the plurality of dynamic surface tension measurements;
   obtaining a second aqueous sample from the well;
   determining the concentration of the target component in the second aqueous sample based on the calibrative dynamic surface tension curves.

2. The method according to claim 1, wherein the background component is selected from the group consisting of an inorganic material, a friction reducer, a scale inhibitor, a biocide, an emulsion breaker, a pour point depressant, a water clarifier, a shale and clay stabilizer, an antifoam, an H2S and O2 scavenger, a corrosion inhibitor, and combinations thereof.

3. The method according to claim 1, wherein the target component is a surfactant.

4. The method according to claim 1, wherein the target component is one selected from the group consisting of nonionic surfactants, ionic surfactants, am photeric surfactants, and combinations thereof.

5. The method according to claim 4, wherein the nonionic surfactant is selected from the group consisting of an ethylene glycol monostearate, a propylene glycol myristate, a glyceryl monostearate, a glyceryl stearate, a polyglyceryl-4-oleate, a sorbitan acylate, a sucrose acylate, a polyethylene glycol (PEG-150) laurate, a polyethylene glycol (PEG-400) monolaurate, a polyoxyethylene monolaurate, a polysorbate, a polyoxyethylene octylphenylether, a polyethylene glycol (PEG-1000) cetyl ether, a polyoxyethylene tridecyl ether, a polypropylene glycol butyl ether, a stearoyl monoisopropanolamide, a polyoxyethylene, a hydrogenated tallow amide, a fatty acid glycerine ester, a sorbitan fatty acid ester, a sucrose fatty acid ester, a polyglycerine fatty acid ester, an alcohol ethylene oxide adduct, a polyoxyethylene alkyl ether, a polyoxyethylene alkyl allyl ether, a polyoxyethylene lanolin alcohol, a polyoxyethylene fatty acid ester, a polyoxyethylene glycerine fatty acid ester, a polyoxyethylene propylene glycol fatty acid ester, a polyoxyethylene sorbitol fatty acid ester, a polyoxyethylene castor oil, a castor oil derivative, a polyoxyethylene lanolin derivative, a polyoxyethylene fatty acid amide, a polyoxyethylene alkyl amine, an alkylpyrrolidone, a glucamide, an alkylpolyglucoside, a monoalkanol amide, a dialkanol amide, a polyoxyethylene alcohol monoamide, a polyoxyethylene alcohol diamide, a alkylamine, and combinations thereof.

6. The method according to claim 1, wherein the target component is an ionic surfactant.

7. The method according to claim 6, wherein the ionic surfactant is an anionic surfactant selected from the group consisting of fatty acid soaps, ether carboxylic acids and salts thereof, alkane sulfonate salts, a-olefin sulfonate salts, sulfonate salts of fatty acid esters, alcohol sulfate ester salts, fatty alcohol ether sulfate salts, alcohol phosphate ester salts, fatty alcohol ether phosphate ester salts, condensates of fatty acids and amino acids, collagen hydrolysate derivatives and combinations thereof.

8. The method of claim 1, wherein determining the concentration of the background component in the second aqueous sample comprises comparing the dynamic surface tension of the second aqueous sample to the calibrative dynamic surface tension curves.

9. The method of claim 1, wherein determining the concentration based on the calibration curve comprises plotting a linear portion of a slope of each of the dynamic surface tension curves versus concentration of the target component.

10. The method of claim 1, wherein the aqueous test solution is a synthetic brine matching the ionic concentration of water from the oil well.

11. The method of claim 1, adjusting the concentration of the target component in the second aqueous sample.

* * * * *